United States Patent
Kuo (10) Patent No.: US 8,630,469 B2
(45) Date of Patent: Jan. 14, 2014

(54) ABNORMAL SKIN AREA CALCULATING SYSTEM AND CALCULATING METHOD THEREOF

(71) Applicant: Solar System Beauty Corporation, Chiai County (TW)

(72) Inventor: I-Ku Kuo, Chiai County (TW)

(73) Assignee: Solar System Beauty Corporation, Chiai County ( * ) Notice: Subject to any disclaimer, the term of this patent is extended or adjusted under 35 U.S.C. 154(b) by 0 days.

(21) Appl. No.: 13/887,489

(22) Filed: May 6, 2013

(65) Prior Publication Data

US 2013/0245400 A1    Sep. 19, 2013

Related U.S. Application Data (63) Continuation-in-part of application No. 12/768,214, filed on Apr. 27, 2010, now Pat. No. 8,515,144.

(51) Int. Cl.
    *G06K 9/00*    (2006.01)
(52) U.S. Cl.
    USPC .......................................... 382/128; 382/162
(58) Field of Classification Search
    USPC ................. 382/100, 110, 128, 162, 164, 286
    See application file for complete search history.

(56) References Cited

U.S. PATENT DOCUMENTS

| | | | |
|---|---|---|---|
| 8,515,144 B2 * | 8/2013 | Kuo ............................ | 382/128 |
| 2004/0267102 A1 | 12/2004 | Skladnev et al. ............. | 600/315 |
| 2006/0210132 A1 | 9/2006 | Christiansen, II et al. .... | 382/128 |
| 2009/0141956 A1 | 6/2009 | Chhibber et al. ............. | 382/128 |
| 2009/0196475 A1 | 8/2009 | Demirli et al. ................ | 382/128 |
| 2011/0040192 A1 | 2/2011 | Brenner et al. ............... | 600/476 |

* cited by examiner

*Primary Examiner* — Andrew W Johns
(74) *Attorney, Agent, or Firm* — WPAT, PC; Justin King (57) ABSTRACT

An abnormal skin area calculating system and a calculating method thereof are provided. The system includes an image capture module, a database, a skin analysis module, and a numerical calculation module. The database pre-stores at least one abnormal skin analysis data. The skin analysis module analyzes and marks an abnormal skin area in a skin image by using the skin analysis data. The numerical calculation module calculates a pixel area of the abnormal skin area graph, and calculates an actual skin area of a human body corresponding to the abnormal skin area graph with an area calibration parameter. The area calibration parameter is pre-stored in the database, or is generated by the numerical calculation module in calculating a transformation relation between a presented calibration length unit and a pixel distance unit according to a calibration object graph in the skin image.

7 Claims, 13 Drawing Sheets

ABNORMAL SKIN AREA CALCULATING SYSTEM AND CALCULATING METHOD THEREOF

CROSS-REFERENCE TO RELATED APPLICATIONS AND PATENTS

This application claims priority as a CIP application based on prior Non-Provisional application Ser. No. 12/768,214, filed Apr. 27, 2010, which is incorporated by reference.

BACKGROUND OF THE INVENTION

1. Field of Invention

The present invention relates to an abnormal skin analysis system and a method thereof, and more particularly to an abnormal skin area calculating system and a method thereof to analyze abnormal parts of skin and calculate an area of the abnormal parts.

2. Related Art

In the prior art, when a dermatologist diagnoses that a patient has an abnormal skin symptom (for example, skin burnt or scalded, spots, horniness, vitiligo, or pore rough), the doctor usually treats the abnormal skin with a low-level laser therapy (LLLT), as the irradiation of the low-level laser on the human skin is harmless, which is a safe and mild treatment.

However, when the dermatologist charges for the medical treatment, the expenses are determined based on the reputation and intuition of the doctor as well as the area of the abnormal skin measured by eyes. The charging standard is completely decided by the doctor with no objective standard. Moreover, the area of the abnormal skin measured by eyes may vary in numerical values and perceptions, the area of the abnormal skin may vary in numerical values and perceptions from estimating distance or range by the naked eye, so that the doctor and the patient may easily come to misunderstandings in medical charge, thereby causing unnecessary medical disputes.

Therefore, it is a problem to be solved by the manufacturer on how to provide an accurate abnormal skin range calculating mechanism.

SUMMARY OF THE INVENTION

In order to solve the above problem, the present invention is directed to a system and method for calculating an actual abnormal skin distribution area.

Accordingly, the present invention provides an abnormal skin area calculating system, which includes an image capture module, a database, a skin analysis module, and a numerical calculation module. The database pre-stores at least one abnormal skin analysis data. The image capture module captures the skin of a human body to generate a skin image. The skin analysis module analyzes the skin image by using the abnormal skin analysis data to obtain an abnormal skin area graph from the skin image. The numerical calculation module calculates a pixel area of the abnormal skin area graph, and calculates an actual skin area of the human body corresponding to the abnormal skin area graph with an area calibration parameter.

In the abnormal skin area calculating system of the present invention, the skin analysis module adjusts the skin image by using color space transformation as RGB color space and HSV color space. By adjusting the saturation and the value in HSV color space, the abnormal skin area graph can be obtained.

In the abnormal skin area calculating system of the present invention, the skin analysis module obtains the abnormal skin area graph by using a method selected from a group of algorithms. This group includes gray level, binarization, boundary extraction, and edge detection, and any combination thereof.

In the abnormal skin area calculating system of the present invention, a calibration object of known dimensions is further disposed in a capturing range of the image capture module, such that the image capture module captures a skin image with a calibration object graph. The numerical calculation module resolves the presented dimensions of the calibration object graph to obtain a calibration length unit, so as to calculate an area calibration parameter of the calibration length unit and a pixel distance unit.

In the abnormal skin area calculating system of the present invention, the area calibration parameter includes a distance from the image capture module to the skin of the human body and a corresponding calibration transformation parameter between the pixel distance unit and an actual distance unit.

Further, the present invention provides an abnormal skin area calculating method, which includes the following steps. An image capture module captures the skin of a human body to generate a skin image. A skin analysis module analyzes the skin image to obtain an abnormal skin area graph in the skin image. A numerical calculation module calculates a pixel area of the abnormal skin area graph. The numerical calculation module calculates an actual skin area of the human body corresponding to the abnormal skin area graph with an area calibration parameter.

In the abnormal skin area calculating method of the present invention, the skin analysis module adjusts the skin image by using the RGB color space transformation or the HSV color space transformation, so as to obtain the abnormal skin area graph.

In the abnormal skin area calculating method of the present invention, the skin analysis module obtains the abnormal skin area graph by using a method selected from a group of algorithms. This group includes gray level, binarization, boundary extraction, and edge detection, and any combination thereof.

In the abnormal skin area calculating method of the present invention, a calibration object of known dimensions is further disposed in a capturing range of the image capture module, and the image capture module captures a skin image with a calibration object graph. The numerical calculation module resolves the presented dimensions of the calibration object graph to obtain a calibration length unit, and calculates an area calibration parameter of the calibration length unit and a pixel distance unit.

In the abnormal skin area calculating method of the present invention, the area calibration parameter includes a distance from the image capture module to the skin of the human body and a corresponding calibration transformation parameter between the pixel distance unit and an actual distance unit.

The present invention has the following efficacies. The system and method of the present invention are used for calculating an accurate abnormal skin distribution area, so as to provide the dermatologists and the patients with a reliable, undisputed, and objective numerical value. The dermatologists can thus establish or provide a reasonable charging standard to the patients according to the numerical value, such that the mutual trust between the dermatologists and the patients is enhanced, and the efficiency of the dermatologists treating the abnormal skin is also improved. Moreover, the system and method of the present invention further integrate the current medical records technology to record the treated skin area and cured skin area of the patient each time, so as to provide the dermatologists with basis data for subsequent treatment on the patients.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Preferred embodiments of the present invention are illustrated in detail below with the accompanying drawings.

Figure 1:
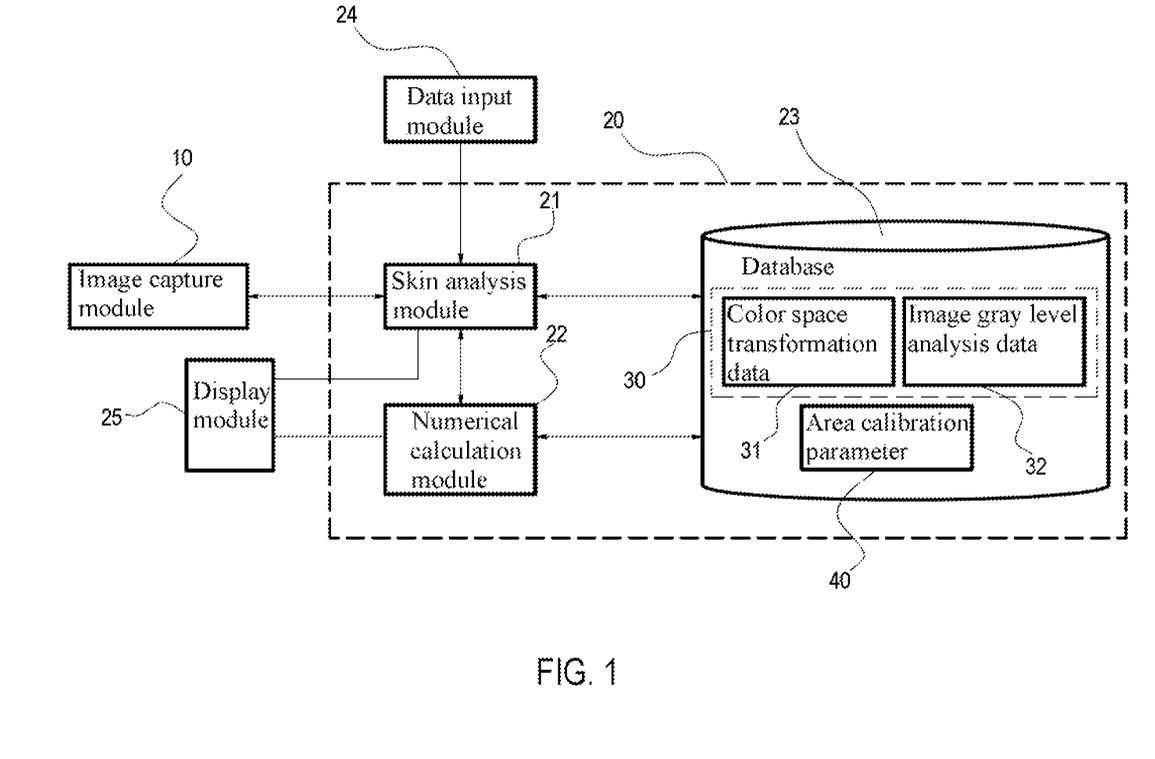
FIG. 1 is a block diagram of an abnormal skin area calculating system according to an embodiment of the present invention.

FIG. 1 is a block diagram of an abnormal skin area calculating system according to an embodiment of the present invention. Referring to FIG. 1, the abnormal skin area calculating system of this embodiment includes an image capture module 10, a database 23, a skin analysis module 21, and a numerical calculation module 22. The system is applicable to an aspect of an electronic apparatus having image capture capability, and also applicable to an aspect of an image capture module 10 linked to a servo host 20. The servo host 20 is a server, the server is a computer device. And the computer device includes a CPU or an IC chip which has the ability for analyzing or calculating. In this embodiment, the aspect of the image capture module 10 linked to the servo host 20 is taken as an example for illustration.

The image capture module 10 captures the skin of a human body to generate a corresponding skin image 51. The image capture module 10 is an image pick-up device such as a video camera, a digital camera, or a hand-held apparatus having image capture capability, and the hand-held apparatus includes a mobile phone or a personal digital assistant (PDA).

The database 23 stores at least one abnormal skin analysis data 30, including various skin features, colors, and abnormal skin. The abnormal skin contains abnormal skin tissue which is the other skin tissue compared with the normal skin, and the abnormal skin tissue is defined as burn, scald, skin and connective tissue diseases, and any skin tissue attempted to improve, etc.

Figure 3A:
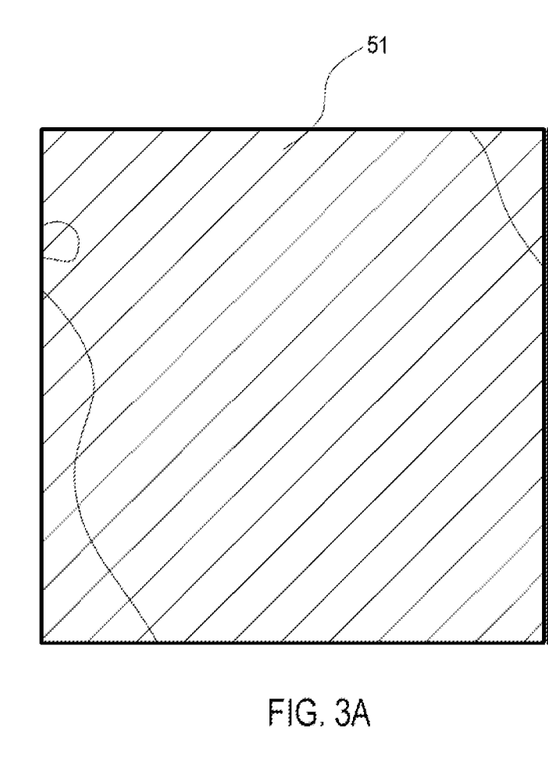
FIG. 3A shows an example of a skin image according to the embodiment of the present invention.
Figure 3B:
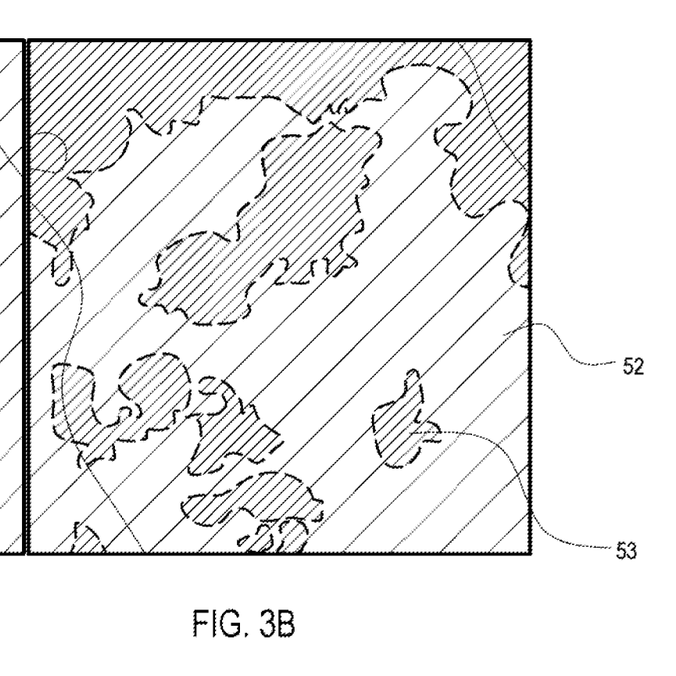
FIG. 3B shows an abnormal skin area graph in FIG. 3A according to the embodiment of the present invention.
Figure 3C:
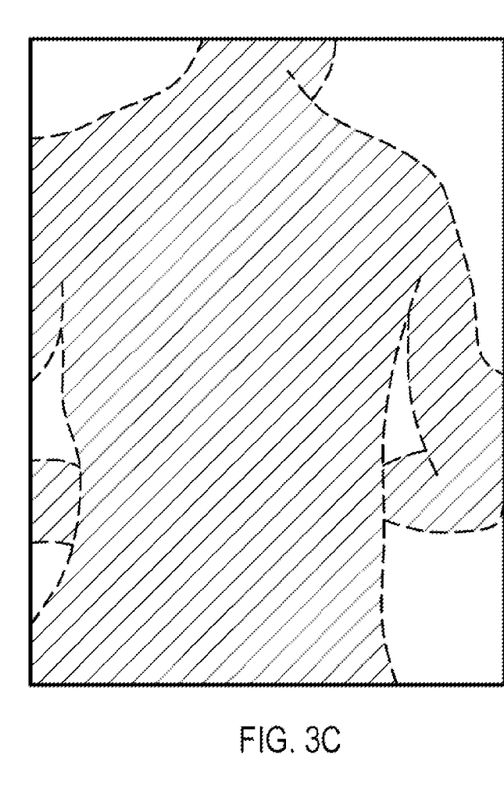
FIG. 3C shows another example of a skin image according to the embodiment of the present invention.
Figure 3D:
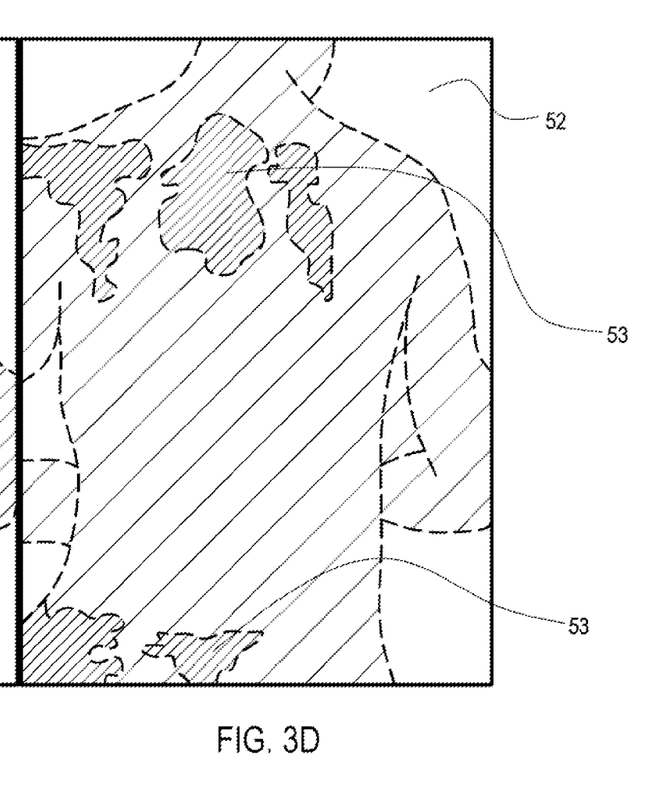
FIG. 3D shows an abnormal skin area graph in FIG. 3C according to the embodiment of the present invention.

Next, referring to FIGS. 3A to 3D, FIG. 3A shows an example of a skin image according to the embodiment of the present invention, FIG. 3B shows an abnormal skin area graph in FIG. 3A according to the embodiment of the present invention, FIG. 3C shows another example of a skin image according to the embodiment of the present invention, and FIG. 3D shows an abnormal skin area graph in FIG. 3C according to the embodiment of the present invention.

The skin analysis module 21 obtains the skin image 51 captured by the image capture module 10, and analyzes the skin image 51 by using the abnormal skin analysis data 30 to obtain an abnormal skin area graph 53 in the skin image 51. The numerical calculation module 22 calculates a pixel area of the abnormal skin area graph 53, and calculates an actual skin area of the human body corresponding to the abnormal skin area graph 53 with an area calibration parameter 40. The skin analysis module 21 and the numerical calculation module 22 can be the CPU or the IC chip.

The abnormal skin analysis data 30 includes more than one color space transformation data 31, which further includes an RGB color space transformation data and an HSV color space transformation data.

The RGB color model in this embodiment is the most commonly used narrative method in descriptive chromatics, and is an additive color mixture model developed based on the three-primary color theory, including three primary colors of red (R), green (G), and blue (B). Each color has a value interval of 0 to 255, and the values of the three colors can be combined to obtain $(256)^3$ colors. The RGB color model may be demonstrated by a three-dimensional (3D) cube, in which an origin of coordinates is (0, 0, 0) representing black, a vertex of coordinates is (255, 255, 255) representing white, three vertexes on the coordinate axes respectively represent the three primary colors of R, G, B, and the remaining three vertexes respectively represent complementary colors of the three primary colors and are respectively obtained by additive color mixture of two adjacent vertexes in the same plane.

It should be noted that, the HSV color system is used for specifying colors based on three basic properties in chromatics, namely, hue (H), saturation (S), and luminance value (V). The hue H is a basic property of colors, and is determined by a rotation angle about a luminance axis (V axis), in which a value of the rotation angle is in a range of 0° to 360°. If it is calculated from red in an anticlockwise direction, red is 0°, green is 120°, and blue is 240°.

The skin analysis module 21 transforms the skin image 51 into a corresponding color image 52 by using one of the above color space transformation data 31. Both the color image 52 in the RGB color space and the color image 52 in the HSV color space are similar to the image shown in FIG. 3B or FIG.

3D. The skin analysis module 21 obtains the color image 52, and adjusts model numerical values in the color image 52 so as to reduce the impact on the subsequent image analysis. For example, if the specification of the color image 52 is the RGB color space, the skin analysis module 21 transforms pixels having excessively white colors in the skin image into colors in the red color system, adopts colors in the green color system to represent pixels having colors in accordance with a normal value (which can be set by a user or stored in the database 23 in advance), and adopts colors in the blue color system to mark pixels having colors that cannot be determined. Other rules may also be adopted, and the present invention is not limited thereto. The rules can be made according to settings of the user or requirements of system designers. For example, if the specification of the color image 52 is the HSV color model, the skin analysis module 21 adjusts the luminance, saturation, and hue of the color image 52, so that the graph presented by the color image 52 may not be too bright or only have a single hue, and thus different colors are presented in accordance with different skin colors.

The skin analysis module 21 resolves the color image 52 to find an abnormal skin distribution area and range, and marks the found area and range to form the abnormal skin area graph 53. At least two resolving methods can be adopted, which are described in the following. In a first method, abnormal skin characteristic data and color data presented on the color image 52 after the color space transformation is completed are stored in the database 23 or included in the abnormal skin analysis data 30, and the skin analysis module 21 uses the data to form a skin analysis operating mode of automatically analyzing the abnormal skin. In a second method, a data input module 24 is a keyboard and is provided and electrically coupled to the skin analysis module 21, so as to input a selection command to click more than one pixel in the color image 52, in which the pixels are regarded as target pixels, and mark pixels having the same color as the target pixels to form a skin analysis operating mode of manually selecting the abnormal skin.

Figure 4A:
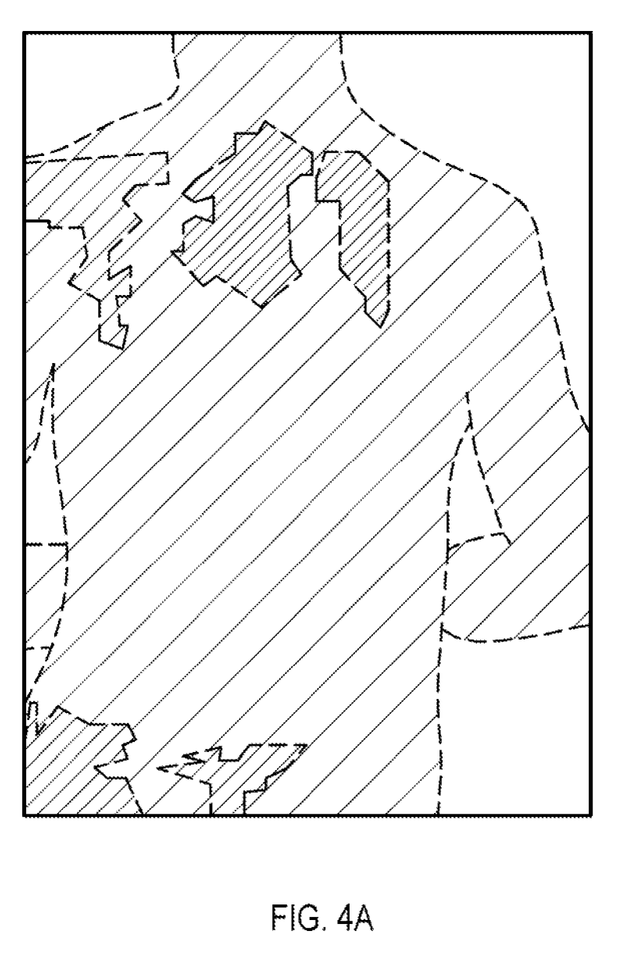
FIG. 4A is a view of gray level transformation image according to the embodiment of the present invention.
Figure 4B:
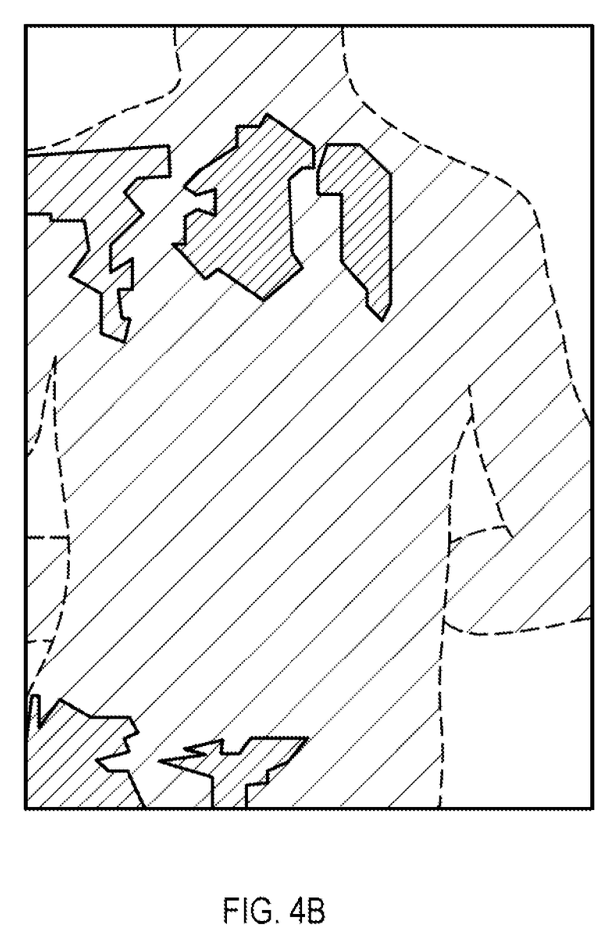
FIG. 4B is a view of image capturing according to the embodiment of the present invention.

FIG. 4A is a view of gray level image transformation according to the embodiment of the present invention, and FIG. 4B is a view of image capturing according to the embodiment of the present invention. Referring to FIGS. 4A and 4B together with FIGS. 3A to 3D for better understanding, in this embodiment, the abnormal skin analysis data 30 may be an image gray level analysis data 32, which records image gray level and a flow control command for analyzing an abnormal skin area image. After transforming the skin image 51 into the color image 52, the skin analysis module 21 transforms the color image 52 into a gray level image 54 according to the image gray level analysis data 32, resolves the gray level image 54 by using an image segmentation method, and marks the abnormal skin area graph 53 in the gray level image 54.

The image segmentation method has several operating modes, which are described in the following.

In a first mode, referring to FIGS. 4A and 4B, a user first inputs a selection command by using the data input module 24, and the selection command includes an image range selected by the user from the gray level image 54. The skin analysis module 21 obtains one or more abnormal pixel sample values from the gray level image according to the selection command, and the user selects an abnormal pixel sample value or the skin analysis module 21 selects an abnormal pixel sample value automatically. Then, the skin analysis module 21 finds a plurality of abnormal pixels in accordance with the abnormal pixel sample value from the gray level image 54 by using the selected abnormal pixel sample value, and marks the abnormal pixels to form the abnormal skin area graph 53.

Figure 5A:
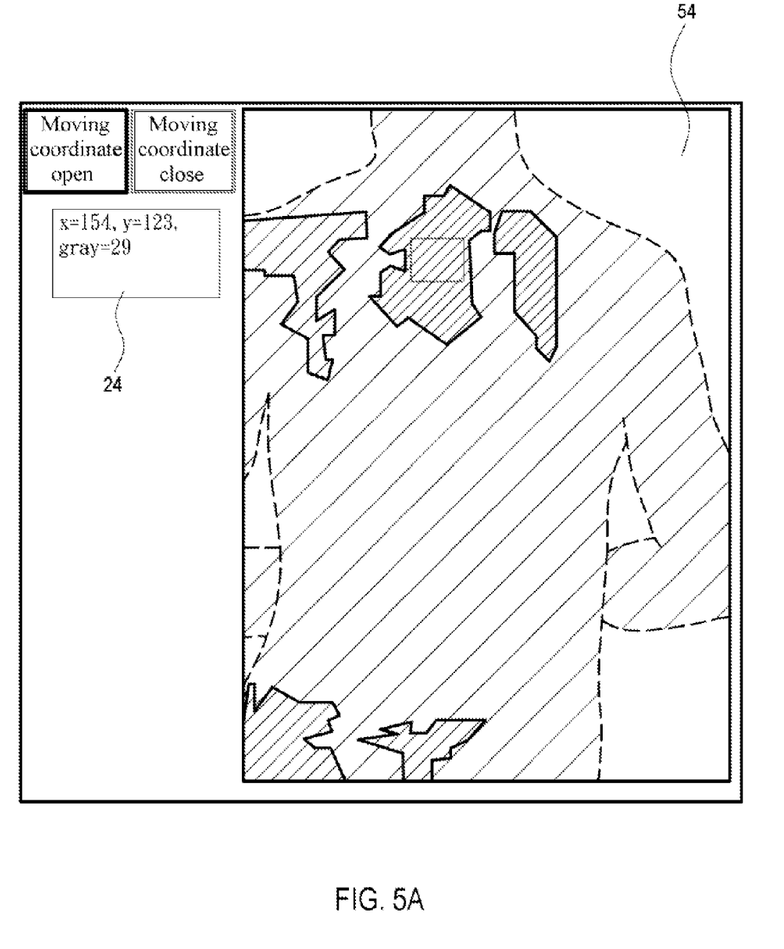
FIGS. 5A and 5B are views of selecting a threshold of a gray level image according to the embodiment of the present invention.
Figure 5B:
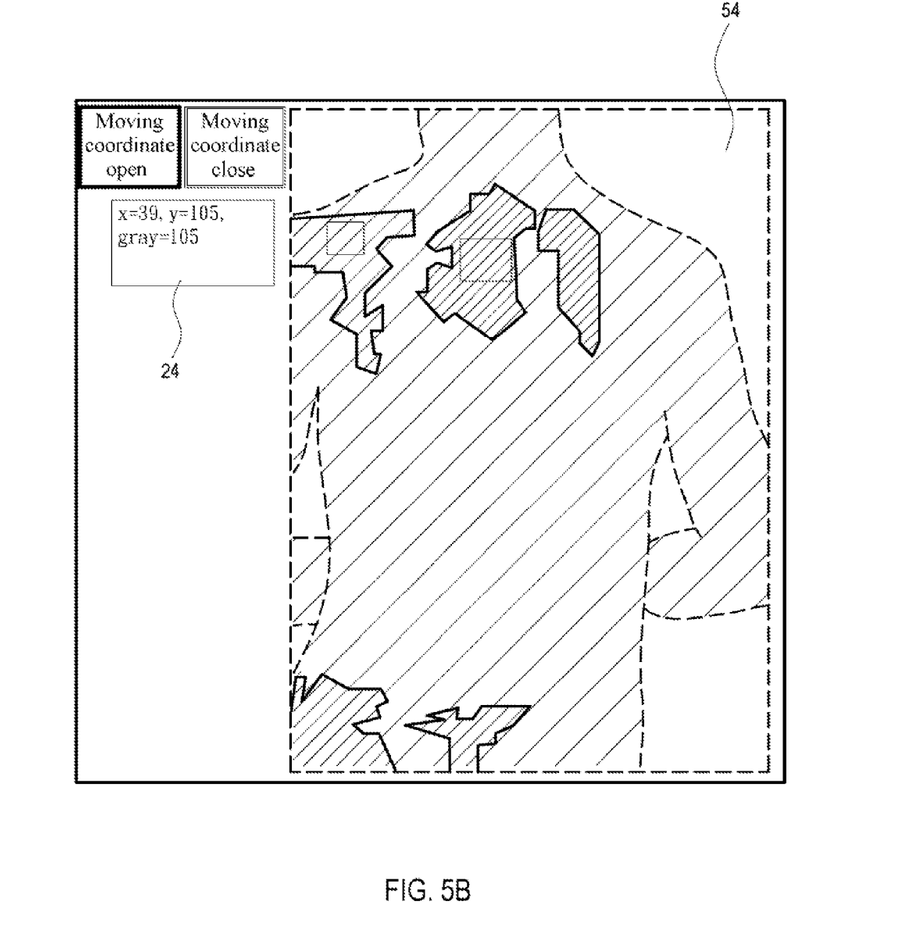
Figure 5C:
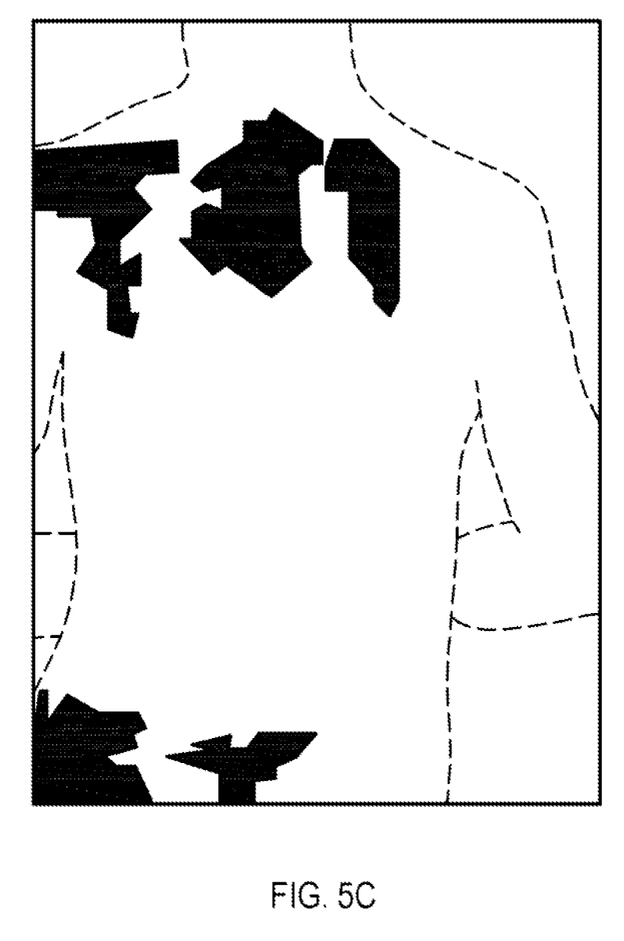
FIG. 5C is a view of forming a binarized image and marking an abnormal skin area graph according to the embodiment of the present invention.

Meanwhile, referring to FIGS. 5A to 5C, FIGS. 5A and 5B are views of selecting a threshold of a gray level image according to the embodiment of the present invention, and FIG. 5C is a view of forming a binarized image and marking an abnormal skin area graph according to the embodiment of the present invention.

In a second mode, the user first inputs a selection command by using the data input module 24, and the selection command includes an image range selected by the user from the gray level image 54 (the part marked by a frame in FIGS. 5A and 5B). The skin analysis module 21 first calculates a threshold corresponding to the gray level image 54. The threshold may be a mean value of pixels in the gray level image 54, or further deduced from a percentage of the mean value (for example, 90%, 80%, 70%, . . . , of the mean value, or the mean value lowered by 10%, 20%, 30%, . . . , and thus similar numerical values, formats, or rules are all applicable). Alternatively, the skin analysis module 21 obtains a threshold from the selected pixel range automatically. Referring to FIGS. 5A and 5B, the skin analysis module 21 respectively calculates two values are 29 and 105. In accordance with the two pixel ranges selected by the user, and deduces a threshold from the gray level values, for example, 105×1.1=115.5, or the user directly assigns the threshold as 110 by using the data input module 24. Other operating modes may also be adopted, and the present invention is not limited thereto. The threshold 110 is taken as an example for illustration below.

The skin analysis module 21 binarizes the gray level image 54 to form a binarized image 55 with the threshold 110, selects from the binarized image 55 a plurality of abnormal pixels (for example, pixels in black or pixels in white, which are selected alternatively), and marks the abnormal pixels to form the abnormal skin area graph 53. The skin analysis module 21 may also obtain the abnormal skin area graph 53 by using edge detection algorithm or boundary extraction algorithm. Further, the skin analysis module 21 may obtain the abnormal skin area graph 53 by combining at least two methods selected from a group of algorithms. This group includes gray level, binarization, boundary extraction, and edge detection.

The area calibration parameter 40 may be generated and implemented in various manners. In one manner, the area calibration parameter 40 includes a distance from the image capture module 10 to the skin of the human body and a corresponding transformation parameter of a pixel distance unit and an actual distance unit, and the area calibration parameter 40 is pre-stored in the database 23.

Figure 6:
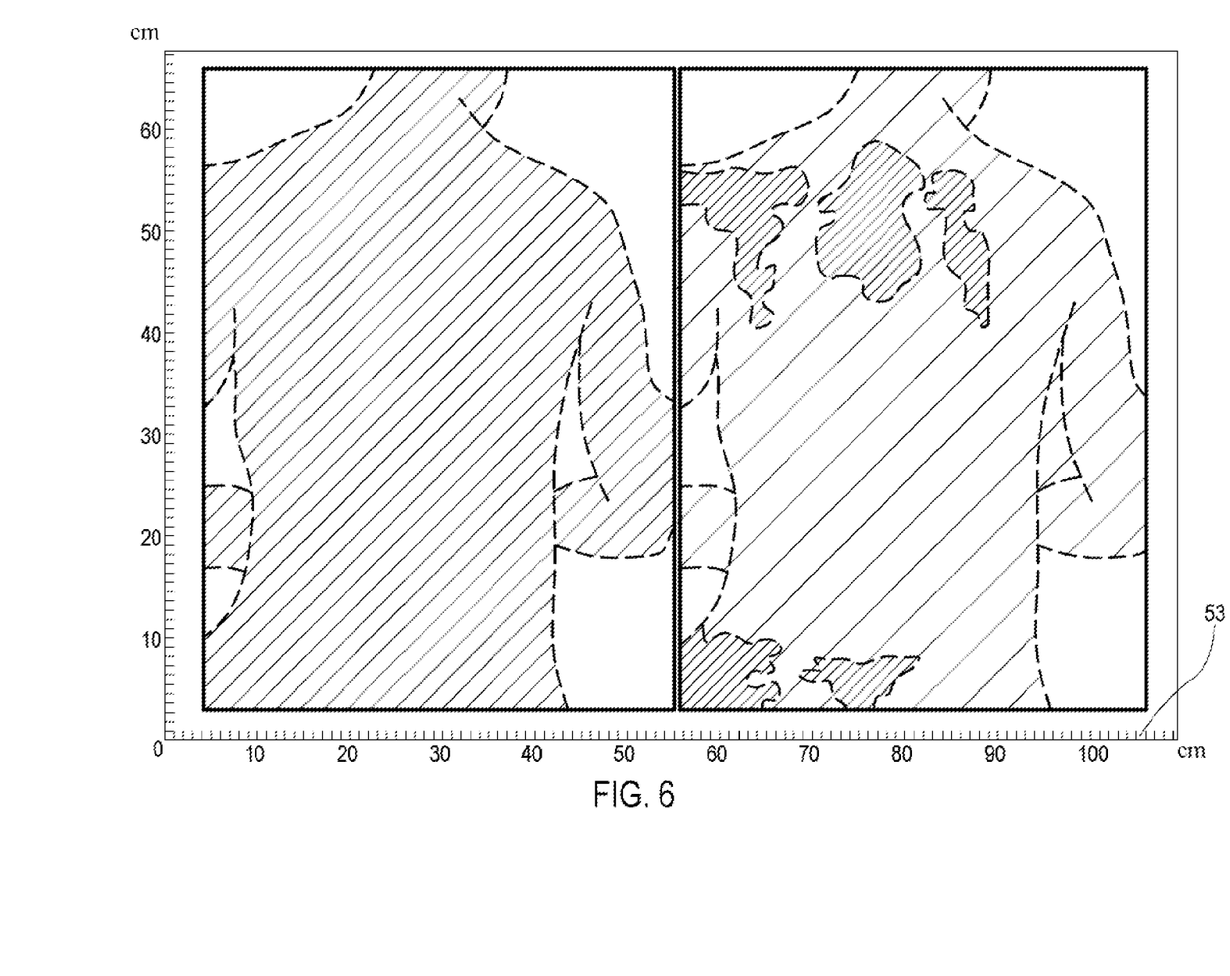
FIG. 6 is a view of an example which is combined a skin image and an abnormal skin area graph therein with an area calibration parameter according to the embodiment of the present invention.

FIG. 6 is a view of an example of combining the skin image 51 and the abnormal skin area graph 53 therein with the area calibration parameter 40 according to the embodiment of the present invention. In an example, when the distance from the image capture module 10 to the skin of the human body is 50 cm, the transformation parameter of the pixel distance unit and the actual distance unit is 10 units: 1 cm. In another example, when the distance from the image capture module 10 to the skin of the human body is 40 cm, the transformation parameter of the pixel distance unit and the actual distance unit is 20 units: 1 cm. In still another example, when the distance from the image capture module 10 to the skin of the human body is 60 cm, the transformation parameter of the pixel distance unit and the actual distance unit is 5 units: 1 cm. Other data modes may also be adopted, and the present invention is not limited thereto. Related data configurations are also applicable.

The distance from the image capture module 10 to the skin of the human body may be obtained in two manners. One is that the image capture module 10 has a distance sensing unit for sensing a distance to the human body, and the other is that the user inputs a distance numerical value by using the data input module 24, such that the numerical calculation module 22 selects an area calibration parameter 40 corresponding to the distance numerical value.

In another implementing manner of the area calibration parameter 40, the user provides a calibration object which is disposed in a capturing range of the image capture module 10. The skin image 51 captured by the image capture module 10 includes a calibration object graph corresponding to the calibration object. The numerical calculation module 22 resolves the calibration object graph to obtain a calibration length unit presented by the calibration object graph, calculates a transformation relation of the calibration length unit and a pixel distance unit, and records the transformation relation as the area calibration parameter 40. The calibration object is an object of known dimensions, for example, a measuring scale, tag, or plate with a known area unit. The plate is polygonal with its edges capable of being engaged together and having the same shape, such as a parallelogram, regular hexagon, or triangle.

All the generating and implementing manners of the area calibration parameter 40 are applicable to the numerical calculation module 22 for calculating the actual abnormal skin distribution area.

In addition, the system includes a display module 25 connected to the skin analysis module 21 and the numerical calculation module 22, and used for presenting a processing procedure and a processing result of the skin image 51. Moreover, the display module 25 also presents an input interface of the data input module 24, and the user can input related parameters and perform related functions through the interface.

Figure 2A:
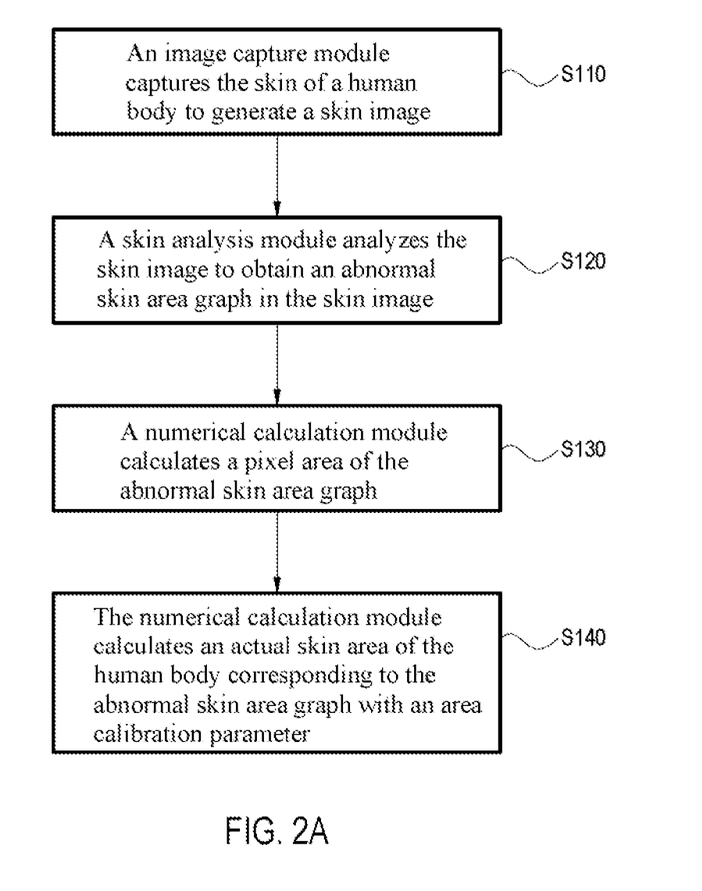
FIG. 2A is a flow chart of an abnormal skin area calculating method according to an embodiment of the present invention.
Figure 2B:
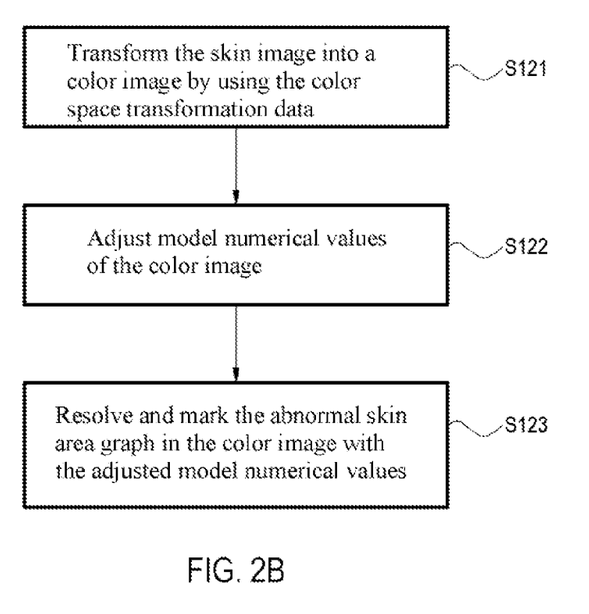
FIG. 2B is a detailed flow chart of Step S120 in the abnormal skin area calculating method according to the embodiment of the present invention.
Figure 2C:
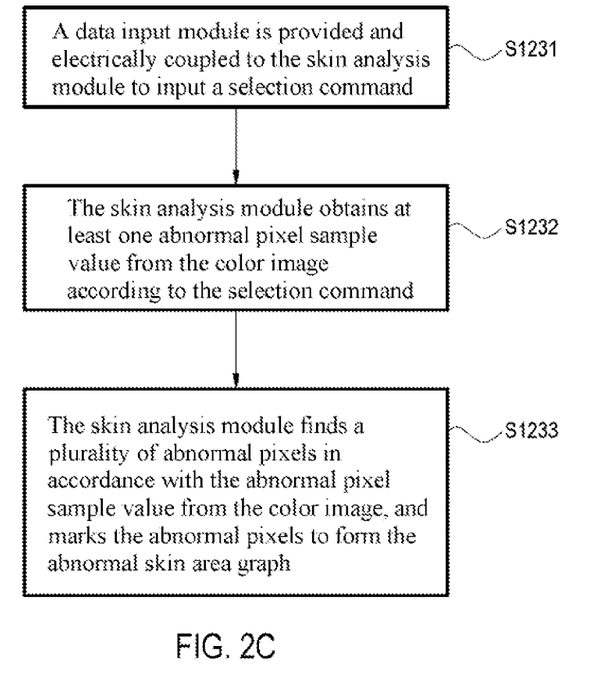
FIG. 2C is a detailed flow chart of Step S123 in the abnormal skin area calculating method according to the embodiment of the present invention.
Figure 2D:
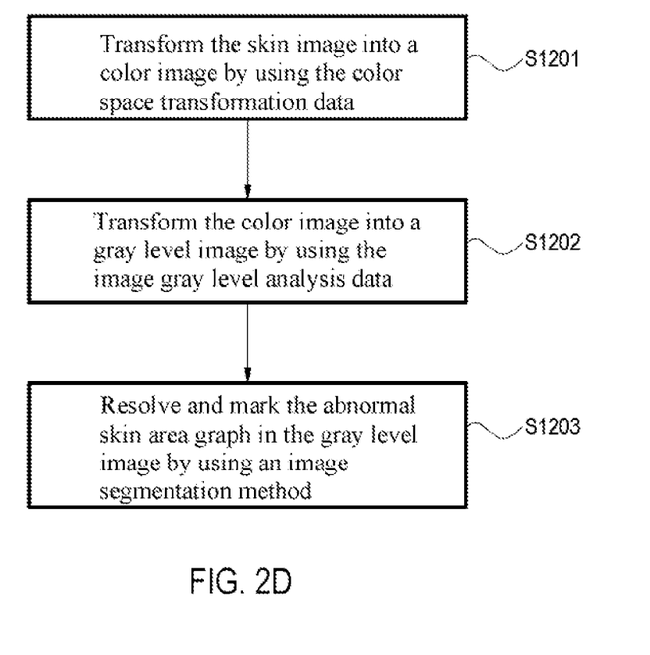
FIG. 2D is another detailed flow chart of Step S120 in the abnormal skin area calculating method according to the embodiment of the present invention.
Figure 2E:
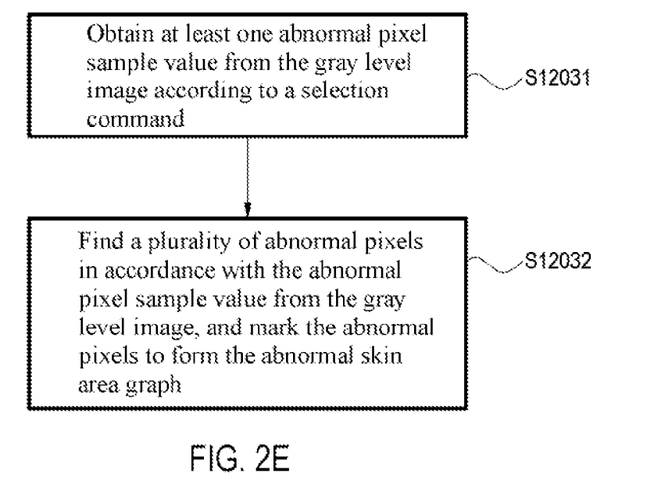
FIG. 2E is a detailed flow chart of Step S1203 in the abnormal skin area calculating method according to the embodiment of the present invention.
Figure 2F:
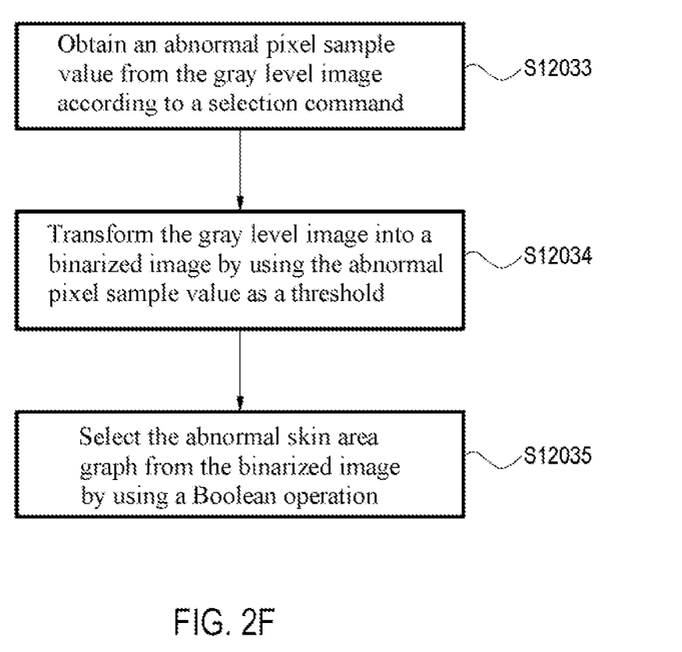
FIG. 2F is another detailed flow chart of Step S1203 in the abnormal skin area calculating method according to the embodiment of the present invention.

FIG. 2A is a flow chart of an abnormal skin area calculating method according to an embodiment of the present invention, FIG. 2B is a detailed flow chart of Step S120 in the abnormal skin area calculating method according to the embodiment of the present invention, FIG. 2C is a detailed flow chart of Step S123 in the abnormal skin area calculating method according to the embodiment of the present invention, FIG. 2D is another detailed flow chart of Step S120 in the abnormal skin area calculating method according to the embodiment of the present invention, FIG. 2E is a detailed flow chart of Step S1203 in the abnormal skin area calculating method according to the embodiment of the present invention, and FIG. 2F is another detailed flow chart of Step S1203 in the abnormal skin area calculating method according to the embodiment of the present invention. Referring to FIGS. 2A to 2F together with FIG. 1 for better understanding, the abnormal skin area calculating method has the following steps.

An image capture module 10 captures the skin of a human body to generate a skin image 51 (Step S110). As described above, the image capture module 10 is an image pick-up device such as a video camera, a digital camera, or a handheld apparatus having image capture capability, which is used for capturing the skin of a human body to generate a corresponding skin image 51.

A skin analysis module 21 analyzes the skin image 51 to obtain an abnormal skin area graph 53 in the skin image 51 (Step S120). The database 23 stores at least one abnormal skin analysis data 30, wherein the abnormal skin contains abnormal skin tissue which is the other skin tissue compared with the normal skin, and the abnormal skin tissue is defined as burn, scald, skin and connective tissue diseases, and any skin tissue attempted to improve, etc. The skin analysis module 21 obtains the skin image 51 captured by the image capture module 10, and analyzes the skin image 51 by using the abnormal skin analysis data 30 to obtain the abnormal skin area graph 53 in the skin image 51.

The abnormal skin analysis data 30 includes more than one color space transformation data 31 or an image gray level analysis data 32, or includes both the data 31 and 32. The color space transformation data 31 includes RGB color space transformation data and HSV space transformation data.

When the abnormal skin analysis data 30 adopts the configuration of the color space transformation data 31, the following detailed process is implemented in Step S120.

Referring to FIG. 2B, the skin analysis module 21 transforms the skin image 51 into a color image 52 by using the color space transformation data (Step S121), and adjusts model numerical values of the color image 52 (Step S122). The skin analysis module 21 transforms the skin image 51 into a color image 52 corresponding to the RGB color space or HSB color space by using one of the color space transformation data 31, in which the skin image 51 is similar to the image shown in FIG. 3B or FIG. 3D.

The skin analysis module 21 adjusts the model numerical values in the color image 52, so as to reduce the impact on the subsequent image analysis. In an example, if the specification of the color image 52 is in the HSV color space, the skin analysis module 21 adjusts the value, saturation, and hue of the color image 52, and the color image 52 presents different colors in accordance with different skin colors. In another example, as pixels in the skin image 51 represent colors in different modes, the skin analysis module 21 transforms the skin image to just show the colors in different modes, thereby simplifying the image and highlighting skin ranges of different symptoms in the color image 52.

The abnormal skin area graph 53 is resolved and marked in the color image 52 with the adjusted model numerical values (Step S123). Referring to FIGS. 3A to 3D, the skin analysis module 21 resolves the color image 52 to find an abnormal skin distribution area and range, and marks the found area and range to form the abnormal skin area graph 53.

At least two resolving methods can be adopted, which are described in the following. In a first method, abnormal skin characteristic data and color data presented on the color image 52 after the color space transformation is completed are stored in the database 23 or included in the abnormal skin analysis data 30, and the skin analysis module 21 uses the data to form a skin analysis operating mode of automatically analyzing the abnormal skin. In a second method, referring to FIG. 2C, a data input module 24 is provided and electrically coupled to the skin analysis module 21, so as to input a selection command (Step S1231) to click more than one pixel in the color image 52. The skin analysis module 21 obtains at least one abnormal pixel sample value from the color image 52 according to the selection command (Step S1232), finds a plurality of abnormal pixels in accordance with the abnormal pixel sample value from the color image 52, and marks the abnormal pixels to form the abnormal skin area graph (Step S1233).

It can be seen from the above step that, the skin analysis module 21 regards the pixels in accordance with the abnormal pixel sample value as target pixels, and marks pixels having the same color as the target pixels to form the abnormal skin area graph, so as to obtain a skin analysis operating mode of manually selecting the abnormal skin.

When the abnormal skin analysis data 30 adopts the configuration of the image gray level analysis data 32, the following detailed process is implemented in Step S120.

Referring to FIG. 2D, the skin analysis module 21 first transforms the skin image 51 into a color image 52 by using the color space transformation data 31 (Step S1201), so as to simplify the subsequent image calculation.

The skin analysis module 21 transforms the color image 52 into a gray level image 54 by using the image gray level analysis data 32 (Step S1202). As described above, the abnormal skin analysis data 30 may also be an image gray level analysis data 32, which records image gray level and a flow control command for analyzing an abnormal skin area image, and the skin analysis module 21 may use the recorded data. The skin analysis module 21 may also directly transforms the skin image 51 into a gray level image by using the gray level analysis data 32. Other similar image gray level modes may also be adopted, and the present invention is not limited thereto.

The skin analysis module 21 resolves and marks the abnormal skin area graph 53 in the gray level image 54 by using an image segmentation method (Step S1203). This step may be implemented in the following two manners, which are described in the following.

In a first manner, referring to FIG. 2E together with FIGS. 4A and 4B, at least one abnormal pixel sample value is obtained from the gray level image according to a selection command (Step S12031). As described above, the user first inputs a selection command by using the data input module 24, and the selection command includes an image range selected by the user from the gray level image 54. The skin analysis module 21 obtains one or more abnormal pixel sample values from the gray level image according to the selection command, and selects an abnormal pixel sample value automatically. Alternatively, the user selects an abnormal pixel sample value from the values obtained by the skin analysis module 21.

The skin analysis module 21 finds a plurality of abnormal pixels in accordance with the abnormal pixel sample value from the gray level image, and marks the abnormal pixels to form the abnormal skin area graph (Step S12032).

In a second mode, referring to FIG. 2F together with FIGS. 5A to 5C, an abnormal pixel sample value is obtained from the gray level image according to a selection command (Step S12033). The user first inputs a selection command by using the data input module 24, and the selection command includes an image range selected by the user from the gray level image 54 (the part marked by a frame in FIGS. 5A and 5B). The skin analysis module 21 calculates one or more values corresponding to the gray level image 54 in the selected image range, and selects a threshold from the calculated values. Alternatively, the skin analysis module 21 calculates a mean value of pixels in the gray level image 54 to serve as the threshold, or further deduces the threshold from a percentage of the mean value (for example, 90%, 80%, 70%, ... , of the mean value, or the mean value lowered by 10%, 20%, 30%, ... , and thus similar numerical values, formats, or rules are all applicable).

The gray level image is transformed into a binarized image by using the abnormal pixel sample value as a threshold (Step S12034). Referring to FIGS. 5A and 5B, the skin analysis module 21 respectively calculates two values are 29 and 105. In accordance with the two pixel ranges selected by the user, and deduces a threshold from the values, for example, 105× 1.1=115.5, or the user directly assigns the threshold as 110 by using the data input module 24. Other operating modes may also be adopted, and the present invention is not limited thereto. The threshold 110 is taken as an example for illustration below.

The abnormal skin area graph is selected from the binarized image by using a Boolean operation (Step S12035). Referring to FIG. 5C, the skin analysis module 21 binarizes the gray level image 54 to form a binarized image 55 with the threshold 110, selects from the binarized image 55 a plurality of abnormal pixels (for example, pixels in black or pixels in white, which are selected alternatively), performs area distribution calculation on the binarized image 55 by using the Boolean operation, and marks the abnormal pixels to form the abnormal skin area graph 53. The skin analysis module 21 may also obtain the abnormal skin area graph 53 by using edge detection algorithm or boundary extraction algorithm. Further, the skin analysis module 21 may obtain the abnormal skin area graph 53 by combining at least two methods selected from a group of algorithms. This group includes gray level, binarization, boundary extraction, and edge detection.

A numerical calculation module 22 calculates a pixel area of the abnormal skin area graph 53 (Step S130). The numerical calculation module 22 first calculates a pixel area of the abnormal skin area graph 53 in the image range by using a related linear or curved calculating formula.

When the skin analysis module 21 analyzes the abnormal skin area graph 53, edge detection algorithm, boundary extraction algorithm, or both of the two algorithms may be introduced to obtain an accurate abnormal skin area graph 53. Other related graphic analysis technologies may also be adopted, and the present invention is not limited thereto.

The numerical calculation module 22 calculates an actual skin area of the human body corresponding to the abnormal skin area graph 53 with an area calibration parameter 40 (Step S140). Referring to FIG. 6, the area calibration parameter 40 includes a distance from the image capture module 10 to the skin of the human body and a corresponding transformation parameter of a pixel distance unit and an actual distance unit. In an example, when the distance from the image capture module 10 to the skin of the human body is 50 cm, the transformation parameter of the pixel distance unit and the actual distance unit is 10 units: 1 cm. In another example, when the distance from the image capture module 10 to the skin of the human body is 40 cm, the transformation parameter of the pixel distance unit and the actual distance unit is 20 units: 1 cm. In still another example, when the distance from the image capture module 10 to the skin of the human body is 60 cm, the transformation parameter of the pixel distance unit and the actual distance unit is 5 units: 1 cm. Other data modes may also be adopted, and the present invention is not limited thereto. Related data configurations are also applicable.

The distance from the image capture module 10 to the skin of the human body may be obtained in two manners. One is that the image capture module 10 has a distance sensing unit for sensing a distance to the human body, and the other is that the user inputs a distance numerical value by using the data input module 24, such that the numerical calculation module 22 selects an area calibration parameter 40 corresponding to the distance numerical value.

In another implementing manner of the area calibration parameter 40, the user provides a calibration object which is disposed in a capturing range of the image capture module 10. The skin image 51 captured by the image capture module 10 includes a calibration object graph corresponding to the calibration object. The numerical calculation module 22 resolves the calibration object graph to obtain a calibration length unit presented by the calibration object graph, calculates a transformation relation of the calibration length unit and a pixel distance unit, and records the transformation relation as the area calibration parameter 40. The calibration object is an object of known dimensions, for example, a measuring scale, tag, or plate with a known area unit. The plate is polygonal with its edges capable of being engaged together and having the same shape, such as a parallelogram, regular hexagon, or triangle.

All the generating and implementing manners of the area calibration parameter 40 are applicable to the numerical calculation module 22 for calculating the actual abnormal skin distribution area. Moreover, the numerical calculation module 22 further calculates by accumulation a total area of a plurality of the abnormal skin area graphs, and calculates an actual distribution area of the abnormal skin according to the area calibration data, so as to make statistics of the total skin area in one or more courses of treatment, thereby providing the user and the patient with a reliable reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An abnormal skin area calculating system, comprising:
   an image capture module, for capturing skin of a human body to generate a skin image;
   a database, for storing at least one abnormal skin analysis data;
   a skin analysis module, for analyzing the skin image by using the abnormal skin analysis data to obtain an abnormal skin area graph in the skin image; and
   a numerical calculation module, for calculating a pixel area of the abnormal skin area graph, and calculating an actual skin area of the human body corresponding to the abnormal skin area graph with an area calibration parameter.

2. The abnormal skin area calculating system according to claim 1, wherein the abnormal skin analysis data comprises a color space transformation data, and the skin analysis module transforms the skin image into a color space by using the color space transformation data, adjusts values of the color image, and resolves and marks the abnormal skin area graph in the color space with the adjusting values.

3. The abnormal skin area calculating system according to claim 2, further comprising a data input module for inputting a selection command, wherein the skin analysis module obtains an abnormal pixel sample value from the color space according to the selection command, finds a plurality of abnormal pixels in accordance with the abnormal pixel sample value from the color space, and marks the abnormal pixels to form the abnormal skin area graph.

4. The abnormal skin area calculating system according to claim 1, wherein the area calibration parameter comprises a distance from the image capture module to the skin of the human body and a corresponding transformation parameter between a pixel distance unit and an actual distance unit, and the area calibration parameter is pre-stored in the database.

5. The abnormal skin area calculating system according to claim 1, further comprising a calibration object disposed in a capturing range of the image capture module, wherein the skin image further comprises a calibration object graph corresponding to the calibration object, the numerical calculation module resolves the calibration object graph to obtain a calibration length unit so as to calculate an area calibration parameter for transforming the calibration length unit and a pixel distance unit, and the calibration object is an object of known dimensions and is a measuring scale, tag, or plate with a known area unit.

6. The abnormal skin area calculating system according to claim 1, wherein the skin analysis module transforms the skin image into a gray level image, deduces a threshold from the gray level image, binarizes the gray level image, adjusts the threshold to find a plurality of abnormal pixels, and marks the abnormal pixels to form the abnormal skin area graph.

7. The abnormal skin area calculating system according to claim 1, wherein the numerical calculation module further accumulates a plurality of the abnormal skin graph areas, and records in the database.

\* \* \* \* \*